(12) United States Patent
Prescher

(10) Patent No.: US 12,416,380 B2
(45) Date of Patent: Sep. 16, 2025

(54) BIOCOMPATIBLE AND/OR FOOD-SAFE TUBE ASSEMBLY

(71) Applicant: RAUMEDIC AG, Münchberg (DE)

(72) Inventor: Jörg Prescher, Ramsthal (DE)

(73) Assignee: RAUMEDIC AG, Münchberg (DE)

( * ) Notice: Subject to any disclaimer, the term of this patent is extended or adjusted under 35 U.S.C. 154(b) by 0 days.

(21) Appl. No.: 18/242,607

(22) Filed: Sep. 6, 2023

(65) Prior Publication Data

US 2024/0084943 A1    Mar. 14, 2024

(30) Foreign Application Priority Data

Sep. 8, 2022   (DE) ................. 10 2022 209 380.1

(51) Int. Cl.
| | |
|---|---|
| *F16L 41/02* | (2006.01) |
| *B29C 45/14* | (2006.01) |
| *F16L 41/03* | (2006.01) |
| *B29L 23/00* | (2006.01) |

(52) U.S. Cl.
CPC ...... *F16L 41/021* (2013.01); *B29C 45/14598* (2013.01); *F16L 41/023* (2013.01); *F16L 41/03* (2013.01); *B29L 2023/22* (2013.01)

(58) Field of Classification Search
CPC ....... F16L 41/021; F16L 41/023; F16L 41/03; F16L 41/08
See application file for complete search history.

(56) References Cited

U.S. PATENT DOCUMENTS

| | | | | |
|---|---|---|---|---|
| 3,232,645 | A * | 2/1966 | Bucks | F16L 41/082 |
| | | | | 285/133.11 |
| 4,312,687 | A * | 1/1982 | Sigworth, Jr. | F24S 80/30 |
| | | | | 264/318 |
| 4,848,801 | A * | 7/1989 | Grabowski | F16L 41/08 |
| | | | | 285/200 |
| 4,998,337 | A | 3/1991 | Tiekink | |
| 5,248,171 | A | 9/1993 | Briet | |
| 6,432,345 | B1 | 8/2002 | Warburton-Pitt | |
| 2017/0146178 | A1* | 5/2017 | Kiest, Jr. | F16L 55/179 |
| 2017/0251612 | A1* | 9/2017 | Turk | F16L 41/08 |

* cited by examiner

*Primary Examiner* — David Bochna
(74) *Attorney, Agent, or Firm* — Smartpat PLC

(57) ABSTRACT

A biocompatible and/or food-safe tube assembly (1) is used to connect at least three tube connectors (A, B, C). A first tube section (2) serves to connect two (A, B) of the at least three tube connectors (A, B, C). A sec-ond tube section (3) opens into the first tube section (2) via an orifice (4) in a casing wall (5) of the first tube section (2). An orifice sealing body (8) delimits the orifice (4) to the inner lumen of the first tube section (2) and to the inner lumen of the second tube section (3). The first tube sec-tion 2 and the second tube section 3 are molded onto the orifice sealing body 8. A core (10) is used for this purpose. The result is a biocompatible and/or food-safe tube assembly that avoids manufacturing problems.

10 Claims, 3 Drawing Sheets

BIOCOMPATIBLE AND/OR FOOD-SAFE TUBE ASSEMBLY

CROSS-REFERENCE TO RELATED APPLICATION

This application claims the benefit of German Patent Application DE 10 2022 209 380.1, filed on Sep. 8, 2022, the contents of which is incorporated in its entirety.

TECHNICAL FIELD

The disclosure relates to a biocompatible and/or food-safe tube assembly for connecting at least three tube connectors.

BACKGROUND

Biocompatible and/or food-safe tube assemblies are generally known, for example as a commercially available T-piece, X-piece or Y-piece.

In the manufacture of known tube assemblies, manufacturing problems arise in the area of an orifice in which one tube section of the tube assembly opens into another tube section of the tube assembly, particularly when the tube assembly is produced by injection molding or by a swaging process.

U.S. Pat. No. 6,432,345 B1 discloses a method for producing a silicone tube assembly.

SUMMARY

It is an object of the present disclosure to further develop a biocompatible and/or food-safe tube assembly of the type mentioned at the outset in such a way that corresponding manufacturing problems are avoided.

According to the invention, this object is achieved by a medical tube assembly as claimed.

The inventor recognized that an orifice sealing body delimiting an orifice helps to avoid manufacturing problems in this area. A first tube section and a second tube section of the tube assembly can be made of plastic.

In particular, the tube assembly can meet ISO 10993 biocompatibility requirements. The tube assembly can also meet FDA (Food and Drug Administration) requirements. The tube assembly can comply with the KTW guideline for drinking water tubes. The tube assembly can meet the requirements for food contact materials in accordance with the food contact materials regulation.

The biocompatible and/or food-safe tube assembly may be used in drug delivery and/or as a medical or pharmaceutical connector. The tube assembly may be part of a catheter device. The tube assembly can also be used in the food industry.

Undesirable burr formation in the region of the orifice can be avoided by using the orifice sealing body. Material deformation, in particular expansion of the tube sections in the region of the orifice, can also be avoided. If the medical tube assembly is produced by injection molding, the tube assembly can be removed more easily from a core. Molding errors, in particular the formation of bubbles in the material of the tube sections, can be avoided. The orifice sealing body can also ensure better force distribution in the tube assembly in the area of the orifice. The result is increased stability of the tube assembly.

A design of the orifice sealing body with a sleeve section along one tube section and a further sealing body section following the other tube section around part of the circumference facilitates the manufacture of the tube assembly, in particular demolding the manufactured tube assembly or a component having the orifice sealing body from a shaping tool.

Configurations of the orifice sealing body such that the further sealing body section has the shape of a semicircular cylinder jacket which, in the region of the orifice, delimits the inner lumen of the first tube section over part of the inner lumen circumference of the inner lumen has proven particularly effective in ensuring a problem-free manufacturing process. This applies in particular if the further sealing body section in the region of the orifice delimits the inner lumen of the first tube section over half of the inner lumen circumference of the inner lumen.

Embodiments having a T-piece, a Y-piece, or an X piece have proven themselves in practice. With the "X-piece" design, two orifice sealing bodies can be used, each of which delimits one of the orifices towards the inner lumen of the tube sections.

Silicone material has proven itself for the medical/pharmaceutical application of the tube assembly for both the tube sections and the orifice sealing body.

A Shore hardness of the orifice sealing body being greater than a Shore hardness of the tube sections leads to improved stability of the medical tube assembly in the area of the orifice.

A Shore hardness of the orifice sealing body between 50 Shore-A and 80 Shore-A has proven itself in practice. The Shore hardness of the orifice sealing body can be greater than 60 Shore-A and can also be greater than 70 Shore-A.

Another object of the present disclosure is to provide a method of injection molding or swaging a biocompatible and/or food-safe tube assembly that is effective in terms of material usage. This object is achieved by a method which includes: providing an injection molding or swaging core for defining the inner lumens of the tube sections; connecting the orifice sealing body to the core in the area of the orifice of the medical tube assembly to complete an injection core to be overmolded; inserting the core with the orifice sealing body in an injection molding or swaging die; overmolding the core and the orifice sealing body with flowable material of the tube sections in the die; and pulling the core.

It was recognized that with this method it is possible to completely define the inner lumen of the tube sections by means of the core, apart from the area directly surrounding the orifice, where the inner lumen is delimited by the orifice sealing body. The orifice sealing body can then be designed to save material, which can also offer advantages in terms of the pulling options for the core. In particular, the core can be mechanically connected to a molding tool with which the method is carried out. The result can be a reduction in the effort required to carry out the method.

The advantages of an injection molding process or swaging process correspond to those which have already been explained above in connection with the medical tube assembly.

The core can be made of metal. The core can comprise several parts. The orifice sealing body and the core together represent a group of components overmolded in the overmolding step, with the orifice sealing body and the tube sections being firmly connected to one another after the overmolding, so that when the core is pulled only the core but not the orifice sealing body is pulled.

An embodiment of the invention is explained in more detail below with reference to the drawings.

DETAILED DESCRIPTION

Figure 1:
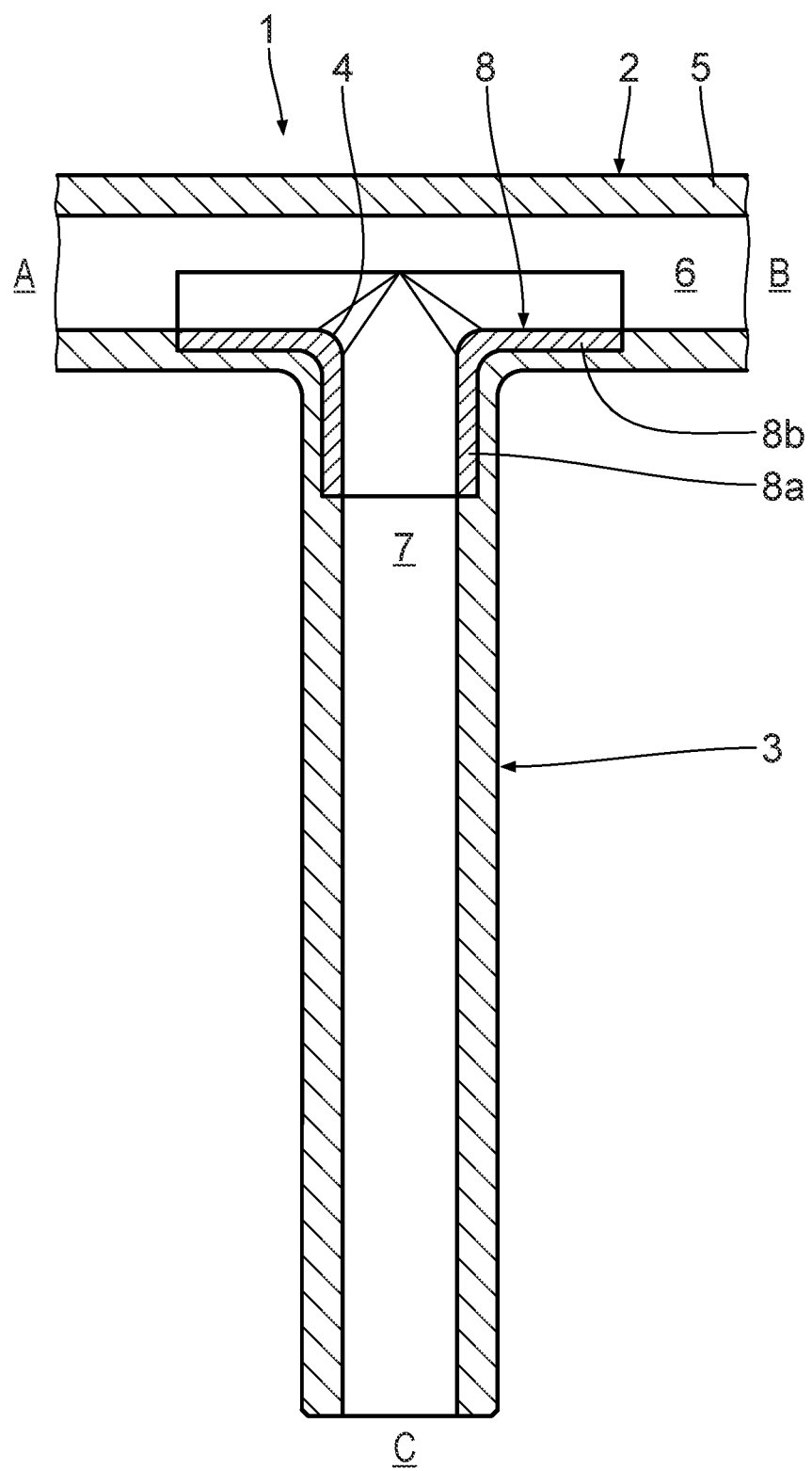
FIG. 1 shows a longitudinal section through a biocompatible and/or food-safe tube assembly for connecting at least three tube connectors, designed as a T-piece.

A biocompatible and/or food-safe tube assembly 1 is used to connect at least three tube connectors, which are not shown in detail in the drawing and are symbolized by the markings "A", "B" and "C." The tube assembly 1 can be used in the clinical area, in the medical/pharmaceutical laboratory environment or also when filling pharmaceutical fluids. The tube assembly 1 can be used, for example, in drug delivery and/or as a medical/pharmaceutical connector. Another possible application of the tube assembly 1 is in the food industry, for example when filling liquid or also highly viscous food masses, such as pureed/pasty masses.

The tube assembly 1 is biocompatible and food-safe.

The tube assembly 1 has a first tube section 2 for connecting the two tube connectors A and B. A second tube section 3 of the tube assembly 1 is used for connecting the third tube connection C. The second tube section 3 opens out via an orifice 4 in a casing wall 5 of the first tube section 2 into the first tube section 2.

In the region of the first tube section 2, the tube assembly 1 is not shown in its entirety. The first tube section 2 can be extended much further in the horizontal direction in FIG. 1.

The two tube sections 2, 3 are made of plastic.

The two tube sections 2, 3 are made of silicone material.

The orifice 4 is delimited by an orifice sealing body 8 towards an inner lumen 6 of the first tube section 2 and towards an inner lumen 7 of the second tube section 3.

Figure 2:
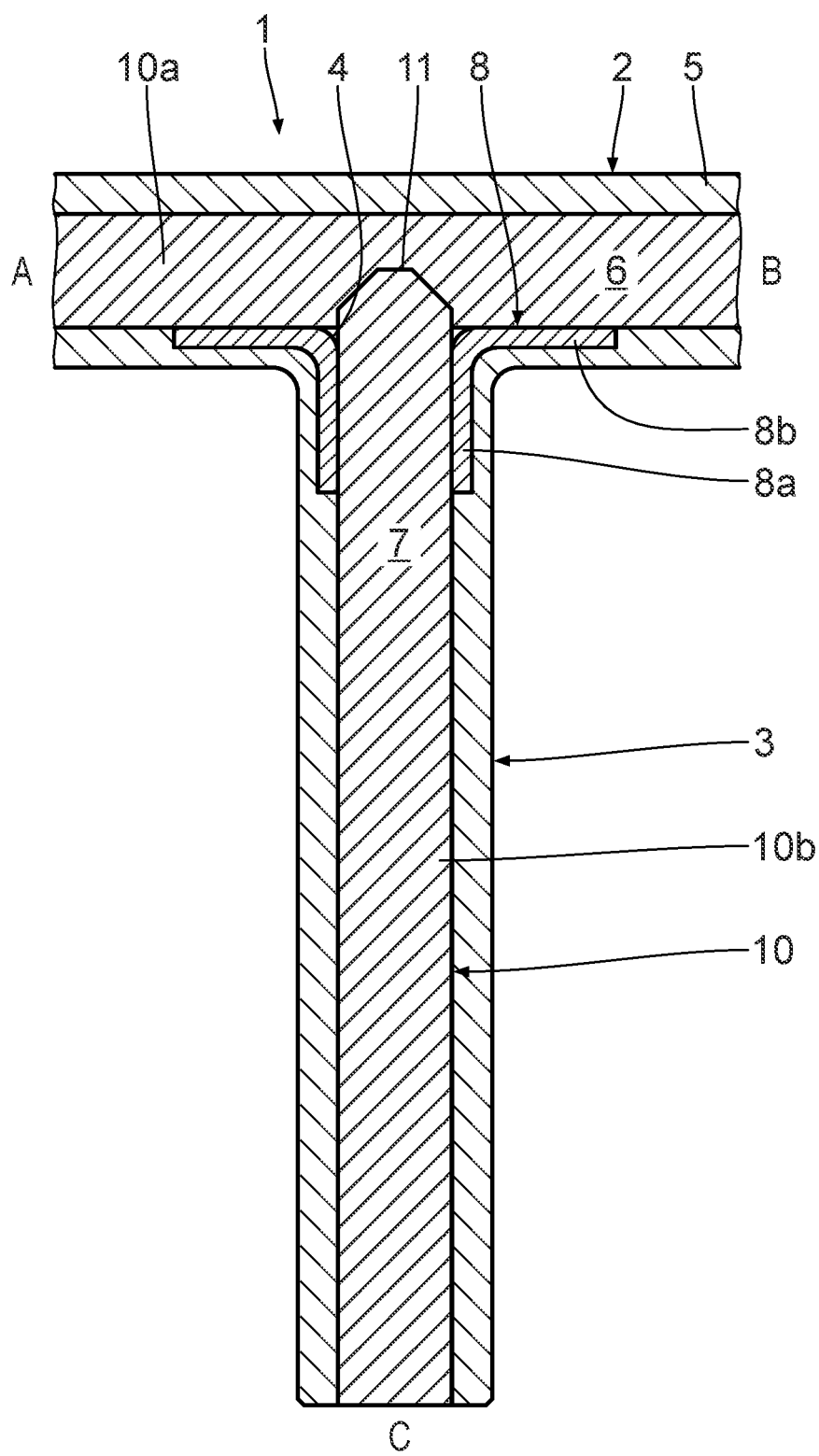
FIG. 2 shows the biocompatible and/or food-safe tube assembly according to FIG. 1 during an injection molding manufacturing process after an overmolding step of a core and before the core is pulled.
Figure 3:
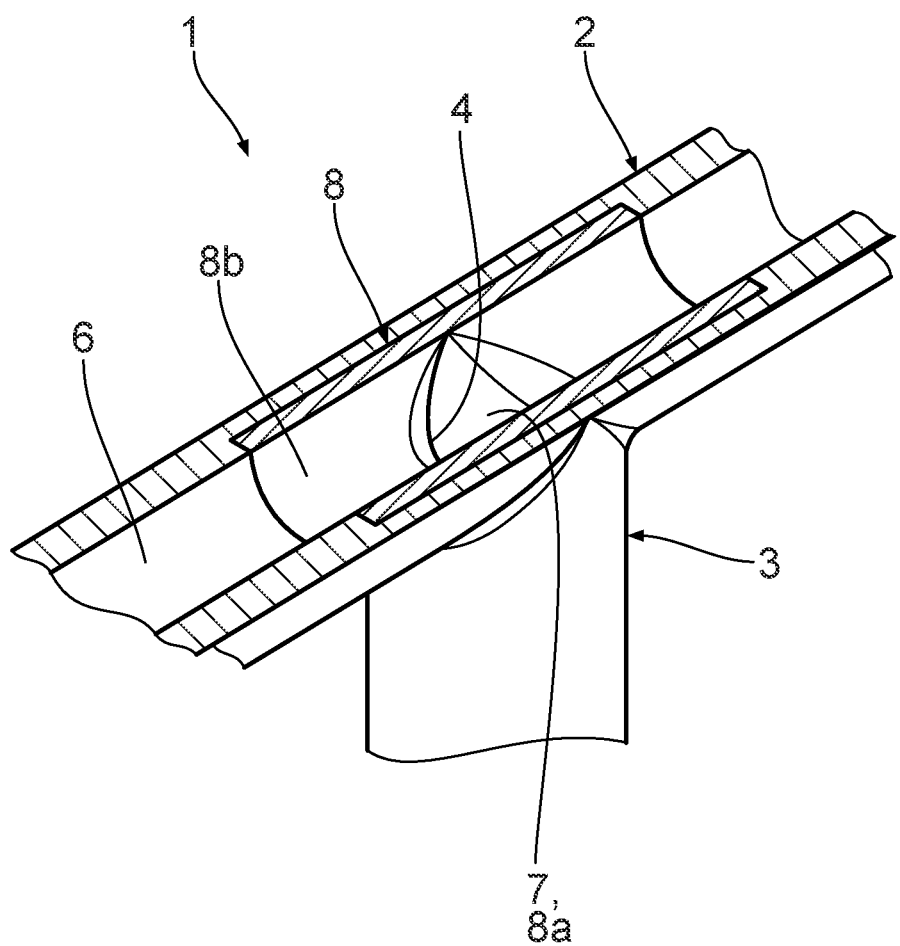
FIG. 3 shows a perspective view of a section of the biocompatible and/or food-safe tube assembly according to FIG. 1 in the area of a T-connection, wherein a first, straight tube section is shown in a longitudinal section with the section axis running perpendicularly compared to FIGS. 1 and 2 so that the view of an orifice sealing body of the tube assembly is unobstructed.

The tube assembly 1 shown in FIGS. 1 to 3 is designed as a T-piece, with the first tube section 2 forming the upper crossbar of the letter "T" and the second tube section 3 forming the stem of the letter "T" perpendicular thereto.

The first tube section 2 and the second tube section 3 are molded onto the orifice sealing body 8.

The orifice sealing body 8 is made of silicone material. A Shore hardness of the orifice sealing body 8 is greater than a Shore hardness of the tube sections 2, 3. The Shore hardness of the orifice sealing body 8 can be in the range between 50 Shore A and 80 Shore A.

The orifice sealing body 8 has a sleeve section 8a which delimits the inner lumen 7 of the second tube section 3 in the region of the orifice 4. Furthermore, the orifice sealing body 8 has a further sealing body section 8b which basically has the shape of a semicircular cylinder jacket and which delimits the inner lumen 6 of the first tube section 2 in the region of the orifice 4 over half of the inner lumen circumference.

The two sections 8a, 8b of the orifice sealing body 8 are integrally formed on each other.

Injection molding the medical tube assembly 1 is performed as follows:

First, a core 10 (see FIG. 2) for defining the inner lumen 6, 7 of the tube sections 2, 3 is provided. The core 10 can be made of metal. The core 10 comprises two parts, with a first core section 10a for defining the inner lumen 6 of the first tube section 2 and with a second core section 10b for defining the inner lumen 7 of the second tube section 3. In the region of the orifice 4, the two core sections 10a, 10b of the core 10 engage in one another in an engagement region 11. When the core 10 is provided, the core section 10a is first placed in a corresponding tool that defines the injection molding volume, and then the core section 10b is pushed into the engagement section 11.

The orifice sealing body 8 is then pushed onto the channel section 10b until it rests against the first channel section 10a of the core 10 via the further sealing body section 8b. Alternatively, before inserting the second core section 10b, the orifice sealing body 8 can first be positioned on the first core section 10a of the core 10 in such a way that the sleeve section 8a is aligned with the engagement region 11 of the core 10. Subsequently, the second core section 10b can be pushed through the sleeve section 8a of the orifice sealing body 8 into the engagement region 11, so that the core 10 is completed.

The injection molding core to be molded around is thus completed over-all, comprising the two core sections 10a, 10b, i.e., the core 10, and the positioned orifice sealing body 8, is then placed in the injection mold of the injection molding tool.

The core 10 and the orifice sealing body 8 are then overmolded with the flowable material of the tube sections 2, 3, i.e., with the silicone material of the tube sections 2, 3, in the injection mold.

After the overmolding and corresponding curing of the initially flowable material of the tube sections 2, 3, first the core section 10b is pulled out of the lumen 7 of the second tube section 3 and then the core section 10a is pulled out of the lumen 6 of the first tube section 2. After removal from the injection mold, the finished tube assembly 1 is then available.

After the overmolding, the orifice sealing body 8 and the tube sections 2, 3 are firmly and permanently connected to one another.

The orifice sealing body 4 ensures that no undesired deformation of the walls of the tube sections 2, 3 takes place in the area of the orifice 4. In particular, an undesired formation of burrs in the area of the orifice 4 can be avoided. Undesirable leakage in the area of the orifice 4 can also be avoided.

In particular, there is no undesired formation of bubbles in the material of the tube sections 2, 3 in the area of the orifice 4.

The biocompatible and/or food-safe tube assembly was described above using a T-piece as an example. The biocompatible and/or food-safe tube assembly can also be designed as a Y-piece. In this case, the first tube section is formed by the two upper branches of the "Y" and the second tube section by the lower tip of the "Y." A further embodiment of the biocompatible and/or food-safe tube assembly can be designed as an X-piece. There are then four tube connectors to be connected. In this case, the first tube section is formed by one of the continuous sections of the "X-piece" variant. The second, crossing tube section of the "X-piece" variant then opens into this continuous tube section via two orifices. Both orifices can then have a corresponding orifice sealing body according to what was explained above in connection with the "T-piece" variant.

What is claimed is:

1. A biocompatible and/or food-safe tube assembly (1) for connecting at least three tube connectors (A, B, C), comprising:
    a first tube section (2) for connecting two (A, B) of the at least three tube connectors (A, B, C);
    a second tube section (3) which opens into the first tube section (2) via an orifice (4) in a casing wall (5) of the first tube section (2); and
    an orifice sealing body (8) which delimits the orifice (4) to an inner lumen (6) of the first tube section (2) and to an inner lumen (7) of the second tube section (3),
    wherein the first tube section (2) and the second tube section (3) are molded onto the orifice sealing body (8) and form a single piece that fully encapsulates the orifice sealing body (8),
    wherein the first tube section (2) and the second tube section (3) are made of silicone, and
    wherein the orifice sealing body (8) comprises
        a sleeve section (8*a*) which extends into the second tube section (3) and
        a further sealing body section (8*b*) which surrounds the orifice (4) and is designed as a partial peripheral sleeve which extends along a part of a circumference of the first tube section (2).

2. The tube assembly according to claim 1,
    wherein the further sealing body section (8*b*) has a shape of a semicircular cylinder jacket which, in a region of the orifice (4), delimits the inner lumen (6) of the first tube section (2) over part of an inner lumen circumference of the inner lumen (6).

3. The tube assembly according to claim 2,
    wherein the further sealing body section (8*b*) in the region of the orifice (4) delimits the inner lumen (6) of the first tube section (2) over half of the inner lumen circumference of the inner lumen (6).

4. The tube assembly according to claim 1, wherein the tube assembly is
    a T-piece,
    a Y-piece, or
    an X piece.

5. The tube assembly according to claim 1,
    wherein a Shore hardness of the orifice sealing body (8) is greater than a Shore hardness of the first tube section (2).

6. The tube assembly according to claim 5,
    wherein a Shore hardness of the orifice sealing body (8) is in a range between 50 Shore-A and 80 Shore-A.

7. The tube assembly according to claim 1,
    wherein the at least three tube connectors (A, B, C) are exactly three tube connectors (A, B, C) forming a T-connection.

8. The tube assembly according to claim 1,
    wherein an inner diameter of the first tube section (2) and an inner diameter of the second tube section (3) are substantially the same.

9. A biocompatible and/or food-safe tube assembly (1) for connecting at least three tube connectors (A, B, C), comprising:
    a first tube section (2) for connecting two (A, B) of the at least three tube connectors (A, B, C);
    a second tube section (3) which opens into the first tube section (2) via an orifice (4) in a casing wall (5) of the first tube section (2); and
    an orifice sealing body (8) which delimits the orifice (4) to an inner lumen (6) of the first tube section (2) and to an inner lumen (7) of the second tube section (3),
    wherein the first tube section (2) and the second tube section (3) are molded onto the orifice sealing body (8) and form a single piece that fully encapsulates the orifice sealing body (8), and
    wherein the orifice sealing body (8) comprises
        a sleeve section (8*a*) which extends into the second tube section (3) and
        a further sealing body section (8*b*) which surrounds the orifice (4) and is designed as a partial peripheral sleeve which extends along a part of a circumference of the first tube section (2), and
    wherein the orifice sealing body (8) is made of silicone.

10. A method for injection molding a biocompatible and/or food-safe tube assembly (1) for connecting at least three tube connectors (A, B, C), including
    a first tube section (2) for connecting two (A, B) of the at least three tube connectors (A, B, C),
    a second tube section (3) which opens into the first tube section (2) via an orifice (4) in a casing wall (5) of the first tube section (2), and
    an orifice sealing body (8) which delimits the orifice (4) to an inner lumen (6) of the first tube section (2) and to an inner lumen (7) of the second tube section (3),
    wherein the first tube section (2) and the second tube section (3) are molded onto the orifice sealing body (8),
    the method comprising:
        providing an injection molding core (10) for defining the inner lumen (6) of the first tube section (2) and the inner lumen (7) of the second tube section (3);
        connecting the orifice sealing body (8) to the core (10) in an area of the orifice (4) of the tube assembly (1) to complete a core to be overmolded;
        inserting the core (10) with the orifice sealing body (8) in an injection mold;
        overmolding the core (10) and the orifice sealing body (8) with silicone and thereby forming the tube sections (2, 3) in the injection mold; and
        pulling the core (10).

\* \* \* \* \*